United States Patent [19]

Shea et al.

[11] Patent Number: 5,476,915
[45] Date of Patent: Dec. 19, 1995

[54] METHOD FOR CONTROLLED SYNTHESIS OF POLYMERS

[75] Inventors: Kenneth J. Shea, Irvine; James R. Walker, Downey; Hiude Zhu, Irvine, all of Calif.

[73] Assignee: The Regents of the University of California, Oakland, Calif.

[21] Appl. No.: 268,243

[22] Filed: Jun. 29, 1994

[51] Int. Cl.⁶ .................................................. C08G 79/08
[52] U.S. Cl. ........................... 528/4; 528/391; 528/422; 528/398
[58] Field of Search ........................... 528/4, 391, 398, 528/422

[56] References Cited

U.S. PATENT DOCUMENTS 3,103,537  9/1963  Rutkowski ................................. 528/4

OTHER PUBLICATIONS

Tufariello et al., "The Reaction of Organoboranes with Dimethylsulphonium Methylide." Chem. Com., 1967, pp. 505–506.

Imoto et al., "Polymerization of Carbenoids, Carbenes, and Nitrenes," J. Macromol. Sci.–Revs. Macromol. Chem. (1972), pp. 1–48.

T. Onak, "Organoborane Chemistry," Academic Press, New York, 1975.

Mucha et al., "Crystallization During Polymerization of Diazomethane. I. The Boron Trifluoride Catalyzed Reaction," J. Polymer Sci., vol. 12, 1993–2018 (1974).

Mukaiyama et al., "The Reaction of Trialkylboron and A–Lithobenzyl–2–Pyridyl or Phenylsulfide. A Convenient Method for the Preparation of Alkylbenzenes," Short Comm., vol. 45, p. 2244 (1972).

Tufariello et al., "The Reaction of Trialkylboranes with Dimethyloxosulfonium Methylide," J. Am. Chem. Soc. 88:20, Oct. 20, 1966, pp. 4757–4759.

J. R. Walker, Masters Thesis: "1. Transition Metal Mediated Ring Opening Metathesis Polymerization: Investigations and Application to the Polymerization of Bicyclo[4.3.1] Decene. 2. Synthesis of Macromolecules via the Pepetitive Homologation of Trialkylboranes", Jun. 1993.

Primary Examiner—John C. Bleutge
Assistant Examiner—Mark D. Sweet
Attorney, Agent, or Firm—Poms, Smith, Lande & Rose

[57] ABSTRACT

Living polymer synthesis methods for the synthesis of oligomeric and high molecular weight polymers with low polydispersity are disclosed. The disclosed methods are based on the discovery that the reaction of a ylid with an organoborane at a high ylid:borane ratio and high temperature provides for the synthesis of high molecular weight polymers with low polydispersity.

11 Claims, 5 Drawing Sheets

METHOD FOR CONTROLLED SYNTHESIS OF POLYMERS

This invention was made with Government support under Grant No. CHE-9121852 awarded by the National Science Foundation. The Government has certain rights in this invention.

BACKGROUND OF THE INVENTION

1. Field of the Invention

The present invention relates generally to methods for synthesizing linear macromolecular structures, such as substituted and unsubstituted polyolefin or polymethylene. More particularly, the present invention involves a method which allows one to accurately control polymerization so that linear oligomers and polymers having pre-selected carbon chain lengths can be synthesized. The present invention also relates to methods for synthesizing highly functionalized polymers and block copolymers. Further, the present invention involves the synthesis of polymers having a high degree of mono-dispersity.

2. Description of the Related Art

Linear polymers, such as polyethylene and poly(methylmethacrylate), are commonly formed by polymerization of their respective ethylene and methylmethacrylate monomers. The general polymerization reactions for these two polymers are set forth in equations A and B.

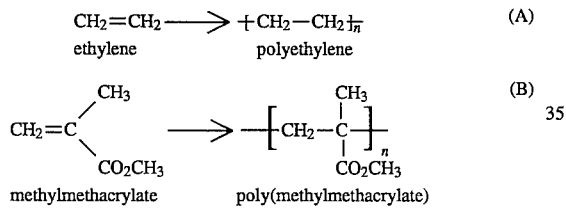

The above polymerization reactions are typically catalyzed with a catalyst such as a Ziegler-Natta catalyst. These polymerization reactions are also commonly initiated with a free radical, nucleophile or electrophile. The existing catalyzed or free radical polymerization reactions are capable of producing oligomers and polymers having chain lengths where n ranges from 50 to hundreds of thousands.

One problem with the present polymerization procedures is that it is difficult to accurately control the length of the polymer chain that is produced during the polymerization reaction. The chain length of the polymer may be controlled somewhat by varying reaction conditions. However, the reaction mechanisms inherent in catalyzed or free radical initiated polymerization reactions makes it extremely difficult to achieve more than qualitative control over the molecular weight, i.e., chain length, of the resulting polymer.

The polymer products produced by the above conventional polymerization reactions tend to include individual polymers which vary widely in chain length. In many situations it is desirable to have a polymer product with this high degree of dispersity. However, there are also many instances where it would be desirable to produce a polymer product which has a low degree of dispersity with respect to polymer chain length. Such polymer products having relatively uniform polymer molecular weight are useful in applications, such as optic devices, and any application where control of molecular weight and functionality is important.

Another problem with existing polymerization procedures is that highly functionalized polymers are difficult or impossible to prepare. For example, polymerization of many 1,2-disubstituted olefins is unknown or difficult. Stilbene and dimethyl fumarate are examples of two disubstituted olefin monomers which are difficult to polymerize using conventional catalytic or free radical polymerization protocols.

In view of the above problems with conventional polymerization procedures, there is a continuing need to develop new approaches for synthesizing polymers where chain length can be accurately controlled and the polydispersity of the resulting polymer product minimized. In addition to these goals, it would also advantageous if the new polymer synthesis procedure could also be used to synthesize highly functionalized polymers.

In many instances it is desirable to add a single carbon atom to an existing carbon atom or chain. One procedure which has been used to add single carbon atoms to a carbon chain is based upon homologation technology. Tefariello et al. (J. Am. Chem. Soc. 88:4757,1966) discloses an example of a homologation process in which a single carbon atom is added to an alkyl group of an alkyl borane by reaction with a ylid by reacting the ylid with a trialkyl borane. An important requirement for this type of homologation procedure is that the reaction conditions be carefully controlled to prevent multiple homologation. In general, these homologation processes are carried out at temperatures of around 0° C. and include equal molar amounts of the ylid and trialkyl borane in order to prevent multiple homologation reactions from occurring.

SUMMARY OF THE INVENTION

In accordance with the present invention, a method is presented for synthesizing linear polymers wherein the ability to control the number of carbon atoms (i.e. length) of the resulting polymer chains is provided. The method is useful in producing polymer products which have a minimum amount of polydispersity. In addition the method is useful in synthesizing α,ω-functionalized polymers and polymers containing main chain functionality on every carbon atom.

The present invention is based on the discovery that homologation reactions can be controlled via temperature and reactant concentrations to provide polyhomologation reactions which are well suited for synthesizing a wide variety of substituted and unsubstituted linear polymers. As a feature of the present invention, it was discovered that the chain length of the polymer product produced during high temperature polyhomologation is determined by and can be accurately controlled through the use specific ratios of ylid and borane reactants.

The polyhomologation method of the present invention not only allows synthesis of polymer chains having a specific chain length, but the polydispersity of the resulting product is low. The method is also well suited for making a variety of substituted and unsubstituted linear polymers. In addition, the method can be repeated using different ylids to form block copolymers.

The above discussed and many other features and attendant advantages of the present invention will become better understood by reference to the following detailed description of the invention.

DETAILED DESCRIPTION OF THE INVENTION

Figure 1:
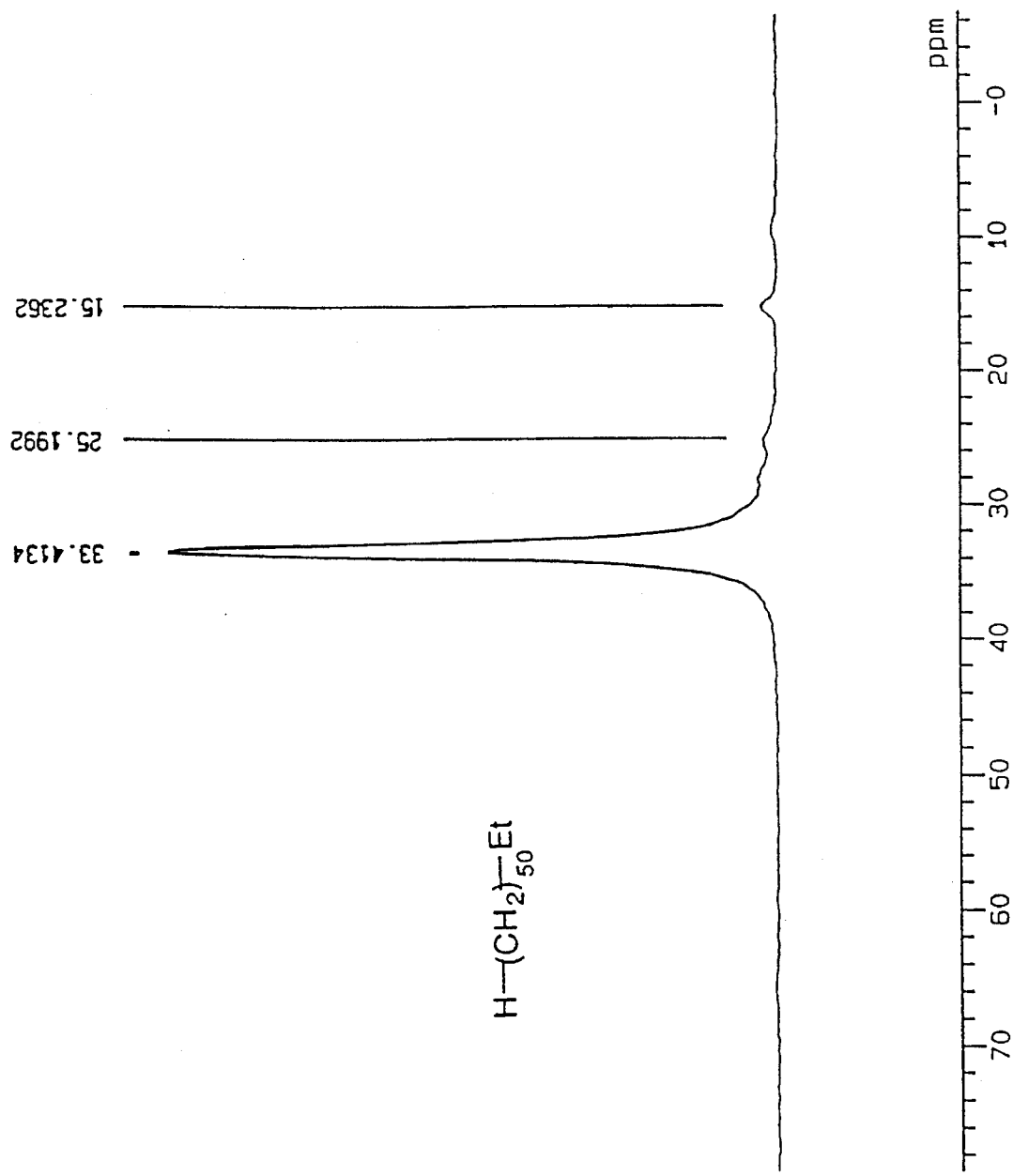
FIG. 1 is a $^{13}$CNMR spectrum of a $CH_3(CH_2)_nCH_3$ polymer where n= 50 which was synthesized in accordance with the polyhomologation process of the present invention.

The present invention involves methods for preparing linear polymer structures. These methods utilize polyhomologation as the basic mechanism for preparing oligomers and polymers. It was discovered that polyhomologation can be used to produce a wide variety of linear polymers in such a way that the number of carbon atoms in the polymer backbone can be accurately controlled. The basic polyhomologation mechanism upon which the present invention is based is set forth in equation C.

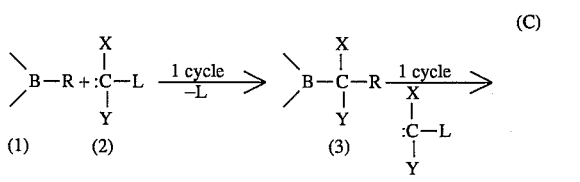

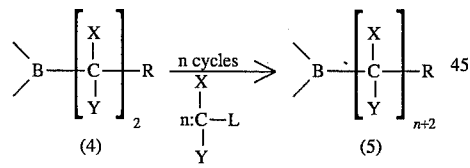

The polyhomologation process starts with an initial homologation reaction between an organoborane (1) and an ylid (2). During the reaction, the alkyl group (R) from the organoborane migrates to the carbon atom of the ylid to produce a reaction product (3). The reaction product (3) is an alkylborane in which the alkyl group (R) has been extended by the one carbon atom provided by the ylid. As shown in equation (C), the homologation of the organoborane is repeated numerous times to form a linear polymer. The length of the resulting linear polymer is determined by the number of homologation cycles n.

The polyhomologation process may be used to produce a wide variety of linear polymers. The number of possible polymers which can be synthesized is only limited by the various organoboranes and ylids which are used as the starting material. Suitable organoboranes include those having the formula:

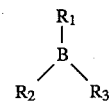

wherein $R_1$, $R_2$, and $R_3$ are a combination of aryl, alkoxy, aryoxy, or alkyl groups containing at least one alkyl group on boron. The alkyl group can be of virtually any composition providing it is compatible with subsequent chemistry. Primary alkyl boranes are preferred. The preferred organoboranes are those which will produce polyolefins. This group of organoboranes includes, but is not limited to, trialkylboranes such as trimethylborane, triethylborane, tri-n-hexylborane, tri-(2,4,4-trimethylpentyl)borane and polymethylenes, di-n-alkyl-thexylborane, n-alkyl-9-BBN, alkyl catecholboranes and related compounds. Triethylborane is a representative organoborane for use in the methods of the present invention.

The particular ylid which is used in the polyhomolgation reaction will also vary depending upon the desired final polymer. Suitable ylids include those having the formula:

wherein X and Y are H, alkyl, aryl, halogen, carbonyl, $CO_2$—R, OR, $NH_2$, SR where R= hydrogen, alkyl, aryl, acetyl; and L is a leaving group capable of being expelled upon migration of the alkyl group from the organoborane to the ylid during the homologation reaction. Suitable leaving groups include dimethylsulfoxide, dinitrogen, halides, amines and phosphines. Exemplary ylid groups include dimethyloxosulfonium methylide, triphenylarsonium benzylide, diazo compounds and sulfur, phosphorus and nitrogen-based ylides.

Other suitable ylid type molecules include compounds having a carbon nucleophile containing an α leaving group having the formula

and carbanions containing an α-leaving group having the formula

where X, Y and L are as defined above.

Examples of polymers which may be prepared using the polyhomologation process in accordance with the present invention include linear polymers having the formula:

$CH_3$—$[CH_2]_n$—$CH_3$ $CH_3$—$[CH_2]_n$—$CH_2$—A

A—$CH_2$—$[CH_2]_n$—$CH_2$—A

A—$CH_2$—$[CH_2]_n$—$CH_2$—B where n= 25 to 100,000 and A and B= OH, NH$_2$, SH, halogen, carbonyl, other organic functional groups such as azides, amides and carbonyl derivates.

Specific exemplary polymers include

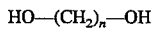
HO—(CH$_2$)$_n$—OH

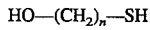
HO—(CH$_2$)$_n$—SH

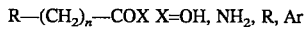
R—(CH$_2$)$_n$—COX  X=OH, NH$_2$, R, Ar

The polyhomologation process is also useful for synthesizing highly substituted linear polymers such as those having the formula:

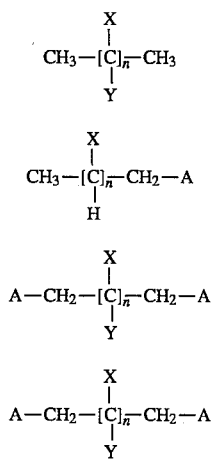

X and Y= H, Aryl, Alkyl, CO$_2$R where R is alkyl or aryl groups having from 1 to 10 carbon atoms; where n=25 to 10,000 and A and B= halogen, carbonyl or other organic functional groups such as azides, amides and carbonyl derivatives, OR, NH$_2$, SR where R= hydrogen, alkyl, aryl, acetyl.

Specific exemplary polymers include

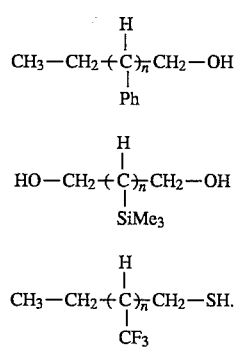

In accordance with the present invention, the number of carbon atoms n in the polymer product is directly related to the initial amounts of organoborane and ylid reactants. In general, the molar ratio of ylid to organoborane will range from 20:1 to 10,000: 1. The length of the polymer product is directly related to the initial molar ratio of ylid to organoborane. As the ratio of ylid to organoborane is increased (i.e. larger relative amount of ylid), the number of carbon atoms in the polymer backbone (i.e. polymer chain length) undergoes a corresponding increase. This relationship between reactant concentrations and final polymer length is used to produce polymers which have a specific length. In addition, the nature of the polyhomologation reaction produces a polymer product which has low polydispersity.

The method may be used to make polymers were n is from 25 to 10,000. The amount of starting ylid and organoborane which is required to make a polymer of a desired length can be determined by routine experimentation. Initially, an approximate target ratio of ylid to organoborane can be established by determining the stoichiometric amounts of each reactant which is required to produce a polymer having the desired carbon chain length, Then, a series of polyhomologations can be carried out using ylid:organoborane ratios which cover the selected target ratio. The molecular weight, i.e. the chain length of the resulting polymer products is measured to establish accurately which specific ylid:organoborane ratio is required to produce the desired carbon chain length.

The temperature at which the polyhomologation polymer synthesis is conducted is an important requirement. Prior homologation processes were intentionally carried out at low temperatures on the order of 0° C. (see Tefariello et al. which was discussed previously)in order to prevent polyhomologation from occurring. In accordance with the present invention, the temperature of the reaction must be kept sufficiently high to insure that polyhomologation occurs. Preferably, the temperature of the reaction will be maintained at levels on the order of 40° C. to 60° C. or higher.

The solvents used to carry out the polyhomologation can be the same as those used in conventional homologation reactions. The polyhomologation procedure can, for the most part, be conducted in the same manner as prior homologation procedures except that the temperature must be kept well above conventional homologation reaction temperatures and the ratio of ylid to organoborane is much higher than the usual equal molar amounts used in conventional homologation reactions. Tetrahydrofuran (THF) is the solvent of choice. Other suitable solvents include toluene or aromatic solvents.

The polymer which is produced by the above described polyhomologation is a polyalkylborane, i.e. the initial boron group from the organoborane is still present in the final polymer. This boron group can be replaced utilizing well known substitution reactions such as reductive or oxidative cleavage of the carbon boron bond.

The polyhomologation method of the present invention is also useful in preparing block copolymers. A virtually unlimited number of block copolymers may be synthesized by carrying out multiple polyhomologations using different ylids. Exemplary block copolymers which can be prepared using the polyhomologation process include:

CH$_3$—(CH$_2$)$_n$—(CD$_2$)$_m$—CH$_3$

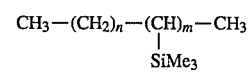

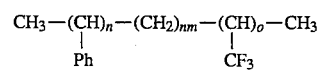

where n= 25 to 10,000 and m= 25 to 10,000.

Highly substituted polymers are easily synthesized by selecting appropriate ylids wherein X and Y are other than H. Examples of substituted polymers which can be prepared using the polyhomologation process of the present invention include:

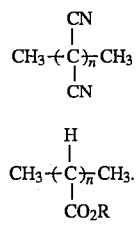

Examples of practice are as follows:

EXAMPLE 1

Synthesis of $CH_3(CH_2)_{50}CH_3$ (50-mer Polymethylene)

The overall process for making polymethylene is set forth below in equations (D) and (E).

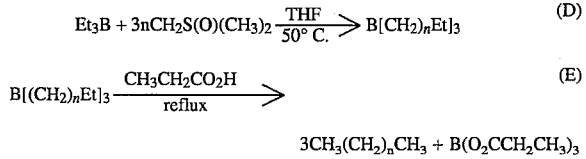

In reaction (D), triethyl borane (the initiator) is combined with trimethylsulfoxonium methylide (the homologating reagent). Triethyl borane is commercially available from companies such as Aldrich Chemical Co. Trimethylsulfoxonium methylide is synthesized from dimethyl sulfoxide which is a common solvent. The synthesis involves two steps. The first step is the synthesis of trimethylsulfoxonium chloride.

Into a 2 liter round bottom flask under $N_2$ was added benzyltributylammonium chloride (91.7 g, 0.294 mol), trimethylsulfoxonium iodide (60.3 g, 0.274 mol), $CH_2Cl_2$ (9.4 L) and deionized water (0.6 L). The mixture was vigorously stirred to allow the solids to dissolve. After stirring overnight at room temperature, the reaction mixture was filtered into a 1 liter separation funnel to give two layers. The top layer (aqueous phase) was collected, washed with $CH_2Cl_2$ (2×150 mL), lyophilized then dried at 85° C. overnight in vacuum oven (~5 mmHg) to provide a crude white solid product. The solid was dissolved in hot methanol (100 mL) and precipitated by adding toluene (100 mL) and cooling in refrigerator. The pure product (30.5 g) was obtained after filtration and vacuum oven drying (~5 mmHg) at 85° C. overnight. The filtrate was left in the refrigerator, filtered and dried to provide additional product (1.8 g). The total yield was 92%. $^1$H NMR (300 MHz, $d_6$-DMSO) δ8.8; IR (KBr): 3448, 2967, 2884, 2361, 1654, 1411, 1342, 1316, 1332, 1047, 962, 766, 668 cm$^{-1}$.

The second step is the synthesis of dimethyloxosulfonium methylide.

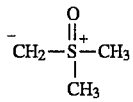

Into a flame dried three neck 500 mL round bottom flask equipped with a stir bar and a condenser was placed NaH (8.74 g, 60% by weight oil dispersion, 219 mmol) against a stream of nitrogen. The NaH was washed with freshly distilled hexanes (3×100 mL) before introduction of freshly distilled THF solvent (150 mL). The trimethylsulfoxonium chloride (25 g), 195 mmol) was then loaded slowly against a nitrogen stream into the reaction flask. After addition of another portion of THF solvent (1 00 mL) by syringe, the reaction mixture was heated to reflux for overnight. The reaction mixture was then transferred by a canula into a schenck flask loaded with celite #545 (3 cm height) and vacuum filtered under nitrogen to provide a clear solution (230 mL). Two parts of this solution (2×10 mL) were added into 50 mL $H_2O$ respectively and titrated with 1N HCl by using phenolphthalein indicator. The concentration of ylid solution was determined to be 0.8N and the yield of the ylid was 94%.

The 50-mer polymethylene was synthesized as follows: into a 250 mL flame dried round bottom flask equipped with a stir bar was added a solution of dimethyloxosulfonium methylide in THF (110 mL, 0.800N, 88.0 mmol) by syringe under nitrogen. A solution of triethylborane in THF (587 μL, 1M, 0.587 mmol) was introduced into the reaction flask at room temperature. This provided a starting ratio of ylid to alkylborane of 50:1. After the installation of a condenser under a stream of $N_2$, the solution was warmed to 50° C. and reaction was monitored until the mixture was not basic (reaction time ~2.5 hours). The basicity of the reaction mixture could be checked by withdrawing an aliquot and adding it to water containing phenolphthalein indicator then observing the color.

Following the reaction, the mixture was concentrated by rotavaporization under $N_2$ protection and the residue dissolved in a deaerated solvent mixture (60 mL, 1:1 by volume) of propionic acid and xylene. The solution was refluxed for 3 days under nitrogen. The mixture was concentrated, dissolved into THF (100 mL) and refluxed again for 0.5 hours. This time, the polymer was precipitated by addition into distilled water (100 mL). The solids were filtered, then washed (water, isopropanol) and vacuum dried (~ 5 mmHg) at 70° C. overnight to provide a white solid polymer (1.23 g, yield: 95.3%). $^1$H NMR (500 MHz, $d_8$-toluene, 100° C.) δ0.88 (t, $CH_3$—$CH_2$—), 1.33 (b, $CH_3(CH_2)_nCH_3$); $^{13}$C solid state NMR (50.29 MHz, CP-MAS, ct 3 ms, pd 1 s, spinning rate 3000 Hz) δ15.4 ($CH_3$—$CH_2$—), 25.3 ($CH_3CH_2$—), 33.2 ($CH_3CH_2(CH_2)_nCH_2CH_3$). The $^{13}$CNMR spectrum is shown in FIG. 1.

EXAMPLE 2

Synthesis of $CH_2(CH_2)_{250}CH_3$ (250-mer of Polymethylene Terminated with Hydrogen)

Figure 2:
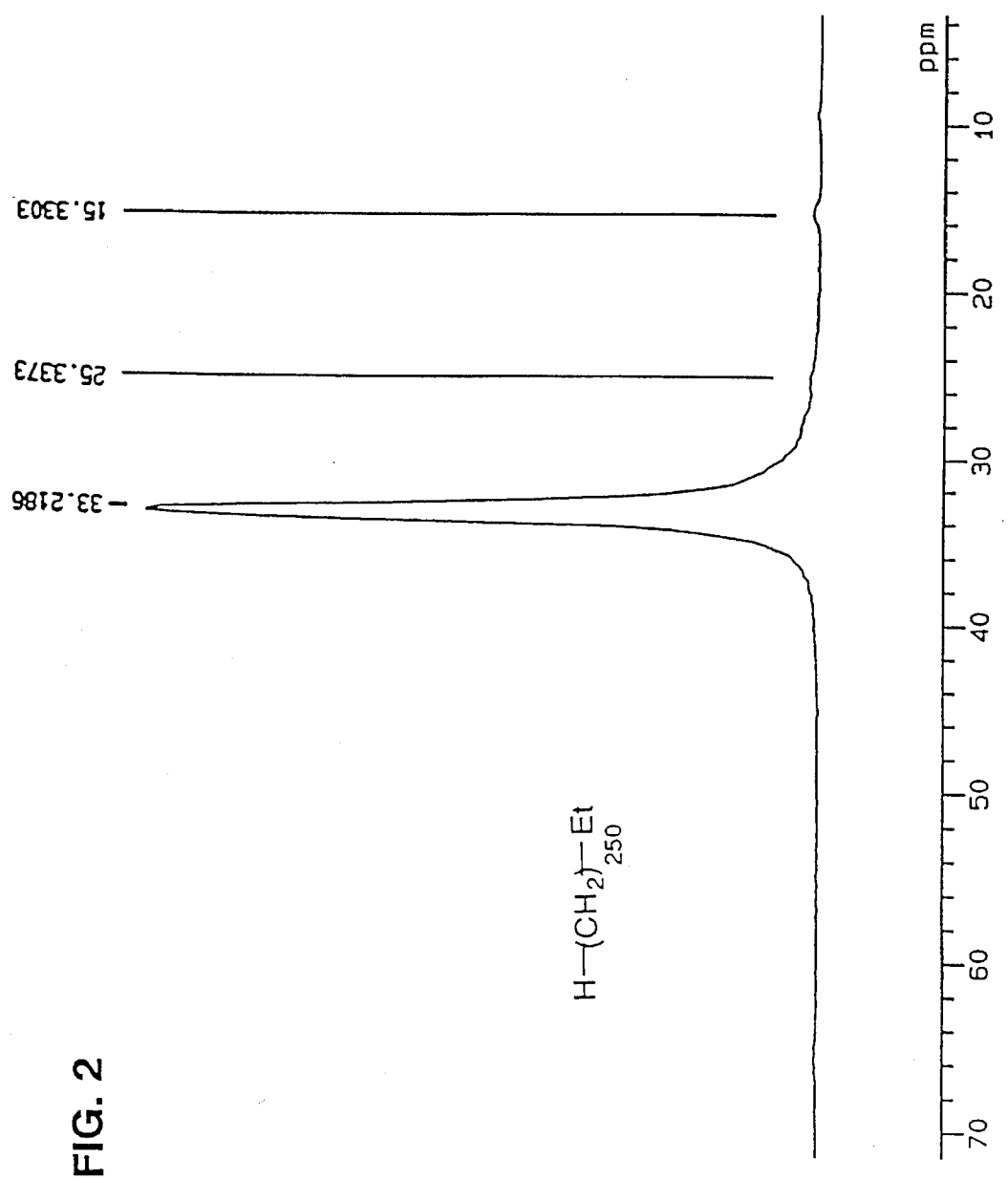
FIG. 2 is a $^{13}$CNMR spectrum of a $CH_3(CH_2)_nCH_3$ polymer where n=250 which was synthesized in accordance with the polyhomologation process of the present invention.

Into a 250 mL flame dried round bottom flask was added a solution of dimethyloxosulfonium methylide in THF (125 mL, 0.721M, 90.1 mmol) under nitrogen. A solution of triethyl borane in THF (0.12 mL, 1.0M, 0.12 mmol) was syringed into the reaction flask at room temperature. This provided an initial ylid to alkyborane ratio of 250: 1. After the installation of a water condenser under a stream of nitrogen, the solution was warmed to 50° C. and reaction was monitored until the mixture was not basic (reaction time ~2.5 hours). The resulted white suspension was concentrated in vacuo, dissolved in a deaerated solvent mixture (48 mL, 1:1 by volume) of propionic acid and xylene then refluxed for 3 days. Afterwards, the mixture was concentrated, dissolved in THF (100 mL), refluxed for 0.5 hours then precipitated by addition to distilled water (100 mL). The solid material was filtered, washed with distilled water and isopropanol then vacuum dried (~5 mmHg) at. 70° C. overnight to provide a white solid polymer (1.20 g, yield: 100%). $^1$H NMR (500MHz, $d_8$-toluene, 100° C.) $\delta$0.88 (t, $CH_3$—$CH_2$—), 1.33 (b, $CH_3(CH_2)_nCH_3$); $^{13}$C solid state NMR (50.29 MHz, CP-MAS, ct 3 ms, pd 1 s, spinning rate 3000 Hz) $\delta$15.3 ($CH_3$—$CH_2$—), 25.3 ($CH_3CH_2$—), 33.2 ($CH_3CH_2(CH_2)_nCH_2CH_3$). The $^{13}$CNMR spectrum is shown in FIG. 2.

EXAMPLE 3

Synthesis of $CH_3(CH_2)_{50}CH_2$—OH (50-mer of Hydroxyl Terminated Polymethylene)

The basic reactions for synthesizing hydroxyl terminated polymethylene is set forth in equations (F) and (G).

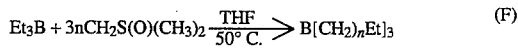

(F)

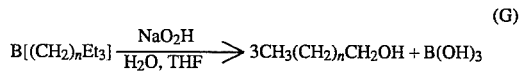

(G)

The first reaction (F) is carried out in the same manner as reaction (D) described above. In reaction (G), the polymerization is terminated by oxidation with basic peroxide to yield the desired long chain alcohol.

Figure 3:
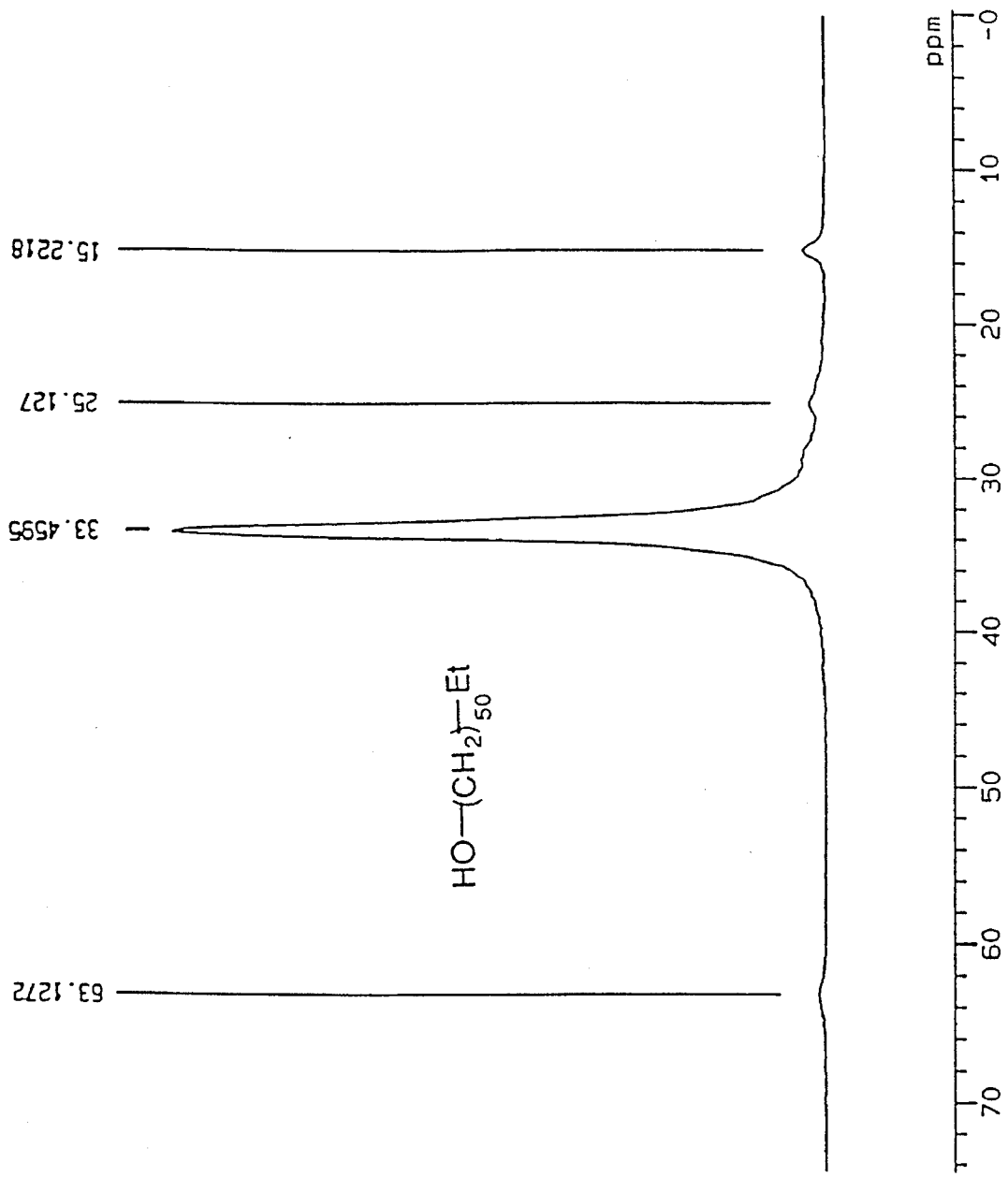
FIG. 3 is a $^{13}$CNMR spectrum of a $CH_3(CH_2)_nCH_2$—OH polymer where n= 50 which was synthesized in accordance with the polyhomologation process of the present invention.
Figure 4:
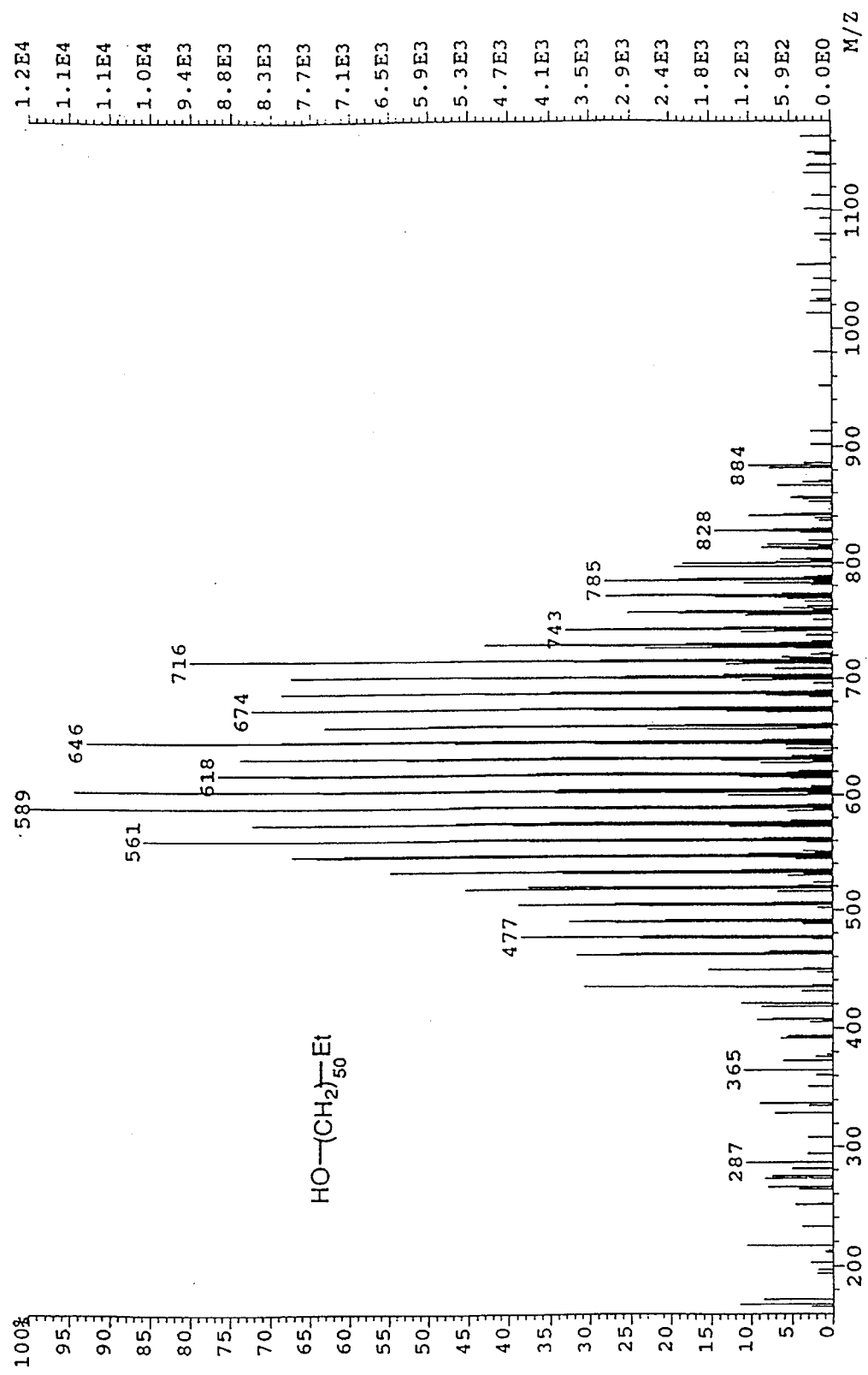
FIG. 4 is a field desorption mass spectrum of the polymer identified in FIG. 3.

The synthesis of the 50-mer hydroxyl terminated polymer is as follows: into a 250 mL flame dried round bottom flask was added a solution of dimethyloxosulfonium methylide in THF (100 mL, 0.8N, 80.0 mmol) by syringe under nitrogen. A solution of triethylborane in THF (533 μL, 1M, 0.533 mmol) was introduced into the reaction flask by syringe at room temperature, then a water condenser was installed. The initial ratio of ylid to borane was 50: 1. The reaction was warmed to 50° C. and reaction was monitored until the mixture was not basic (reaction time ~2.5 hours). After this time, a NaOH solution (4.5 mL, 6N) and hydrogen peroxide (9 mL, 30% by weight aqueous solution) were added to the flask slowly and then the temperature of the reaction mixture was raised to 60° C. After 3 hours, the mixture was cooled and the polymer precipitated by addition to distilled water (150 mL). The solids were vacuum filtered through a coarse silica filter, washed with distilled water then vacuum dried (~5 mmHg) at 70° C. overnight to provide a white solid polymer (1.11 g, yield: 93.3%). $^1$H NMR (500 MHz, $d_8$-toluene) $\delta$ 0.87 (t, $CH_3CH_2$—), 1.32 (b, $CH_3(CH_2)_nCH_2OH$), 3.36 (t, HO—$CH_2$—); 13C solid state NMR (50.29 MHz, CP-MAS, ct 3 ms, pd 1 s, spinning rate 3000 Hz) $\delta$15.2 ($CH_3$—$CH_2$—), 25.1 ($CH_3$—$CH_2$—), 33.5 ($CH_3CH_2(CH_2)_nCH_2OH$), 63.1 ($CH_3CH_2(CH_2)_nCH_2OH$). FIGS. 3 and 4 are $^{13}$CNMR and field desorption mass spectrums, respectively.

EXAMPLE 4

Synthesis of $CH_2(CH_2)_{250}CH_2OH$ (250 Mer of Hydroxyl Terminated Polymethylene)

Figure 5:
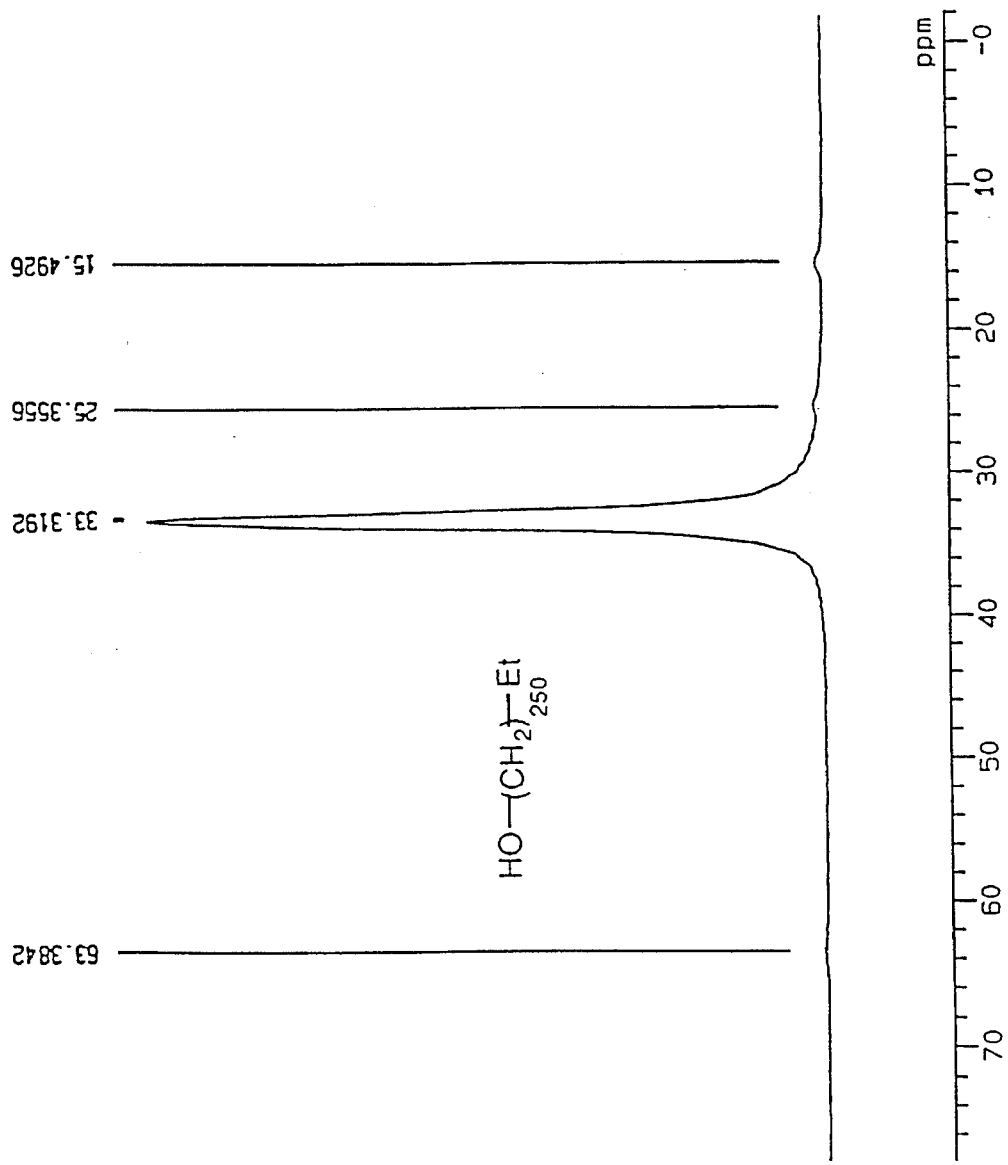
FIG. 5 is a $^{13}$CNMR mass spectrum of a $CH_3(CH_2)CH_2$—OH polymer where n = 250 which was synthesized in accordance with the polyhomologation process of the present invention.

Into a 250 mL flame dried round bottom flask was added a solution of dimethyloxosulfonium methylide in THF (100 mL, 0.721 M, 72.1 mmol) under nitrogen. A solution of triethylborane in THF (96 μL, 1M, 0.096 mmol) was syringed into the reaction flask at room temperature, then a water condenser was installed. This provided an initial ylid to borane ratio of 250:1. The solution was warmed to 50° C. and reaction was monitored until the mixture was not basic (reaction time ~2.5 hours). At this time, a NaOH solution (6N, 0.77 mL) and hydrogen peroxide (1.6 mL, 30% by weight aqueous solution) were added to the flask slowly and then the temperature of the reaction mixture was raised to 60° C. After 3.5 hours, the reaction mixture was cooled and the polymer precipitated by addition to distilled water (100 mL). The solids were vacuum filtered through a coarse silica filter, washed with distilled waster then vacuum dried (~5 mmHg) at 70° C. overnight to provide a white solid polymer (1.02 g, 100%). $^1$H NMR (500 MHz, $d_8$-toluene) $\delta$0.88 (t, $CH_3CH_2$—), 1.33 (b, $CH_3(CH_2)_nCH_2OH$), 3.37 (t, HO—$CH_2$—); $^{13}$C solid state NMR (50.29 MHz, CP-MAS, ct 3 ms, pd 1 s, spinning rate 3000 Hz) $\delta$15.5 ($CH_3$—$CH_2$—), 25.4 ($CH_3$—$CH_2$), 33.3 ($CH_3CH_2(CH_2)_nCH_2OH$), 63.4 ($CH_3CH_2 (CH_2)_nCCH_2OH$); Elemental analysis calculated for $C_{252}H_{506}O$: C, 85.28%; H, 14.27%; Found: C, 84.93%; H, 14.15%. The $_{13}$CNMR spectrum is shown in FIG. 5.

EXAMPLE 5

Synthesis of 48-mer, 98-mer and 196-mer Hydroxyl Terminated Polymethylene

Three additional hydroxyl terminated polymethylene polymers were prepared according to the procedure set forth in Examples 3 and 4. The results of these three syntheses is set forth in the following table:

TABLE 1

Results of Methylene Polyhomologation

| | | |
|---|---|---|
| Ylid:borane molar ratio | 143 | 294 |
| number of insertions/ethyl group, calculated(n)(A) | 48 | 98 |
| average number of insertions observed (DP)(B) | 41 | 67 |
| average Mn(C) | 624 | 896 |
| average MW(D) | 637 | 917 |
| PDI | 1.02 | 1.02 |
| Yield | >99% | 99% |

(A)Number of insertions based on the ratio of the mols of ylid/3× mols of borane.
(B)Based on the observed average molecular weight.
(C)Analysis via field desorption mass spectrometry.
(D)Analysis via field desorption mass spectrometry.

EXAMPLE 6

Synthesis of Poly 1,2 Diphenyl Ethylene

Triphenyl arsonium benzylide is reacted with tri-n-hexylborane in a ratio of 50:1 (150 equivalents of ylide to trialkyl borane). The ylide (1M) and alkyl borane are dissolved in toluene and heated to 60° C. for 24 hours under nitrogen. Propionic acid (1M) was added and the mixture refluxed for 3 days. Polymer was precipitated by addition to MeOH.

EXAMPLE 7

Preparation of

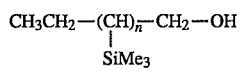

In a manner similar to the preceding examples, trimethylsilydiazo methane (150 equivalents) and triethylborane (1 equivalent) in THF is heated at reflux for 2 days. Following addition of a NaOH solution (4.5 mL, 6N) and hydrogen peroxide (9 mL, 30% by weight aqueous solution) the mixture is then heated to 60° C. After 12 hours, the polymer is precipitated by addition of MeOH.

EXAMPLE 8

Preparation of

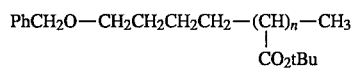

To a solution of catechol borane in THF is added $PhCH_2OCH_2CH_2CHCH_2$. Following hydroboration, t-butyl ethyl diazo acetate (50 equivalents) in THF is added and, after addition of a catalytic amount of $Rh_2(OAc)_4$ or other transition metal, the resultant polymeric organic borane is reacted with propionic acid at reflux. The polymer is precipitated by addition to methanol.

EXAMPLE 9

Preparation of $CH_3-(CH_2)_{50}-(CD_2)_{50}-CH_3$

Synthesis of poly(methylene) (dideuteruromethylene) block copolymer. The synthesis of a "living" $CH_3(CH_2)_{50}$ polymethylene is performed as described in Example 1 (page 12, lines 9–19). Then add the following: "Following the reaction, perdeuterio dimethyloxosulfonium methylide (prepared from $d_6$-DMSO and $CD_3Cl$ by the procedure on page 11 and 12), 88 mmole is added and the reaction is refluxed for an additional 12 hours. The reaction is concentrated, the residue dissolved in 60 mL of propionic acid and xylene (1:1 by volume) and refluxed for 3 days. Following concentration, the polymer is precipitated by addition to methanol.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A method for making a linear polymer, said linear polymer comprising a backbone which comprises between about 25 and 10,000 carbon atoms, said method comprising the steps of:

reacting an amount of ylid with an amount of organoborane at a temperature which is sufficient to cause polyhomologation of said ylid and organoborane to form a polyalkylborane which comprises a carbon backbone having a boron group attached thereto, wherein the ratio of the amount of ylid to the amount of organoborane is selected such that the backbone of said polyalkylborane produced during said polyhomologation comprises between about 25 and 10,000 carbon atoms; and replacing said boron group with a functional group to form said linear polymer which comprises a backbone having from between about 25 and 10,000 carbon atoms.

2. A method for making a linear polymer according to claim 1 wherein the ratio of the amount of ylid to the amount of organoborane is between about 25 to 1 and 10,000 to 1.

3. A method for making a linear polymer according to claim 1 wherein the linear polymer is selected from the group of polymers having a formula:

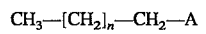

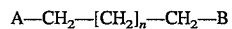

wherein n is from 25 to 25,000; A and B are OH, $NH_2$, SH, halogen, carbonyl or other organic functional group.

4. A method for making a linear polymer according to claim 1 wherein the linear polymer is selected from the group of polymers having a formula:

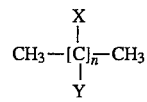

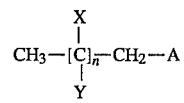

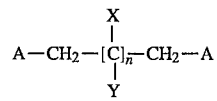

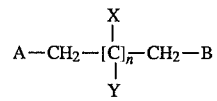

wherein n is from 25 to 10,000; A and B are OH, $NH_2$, SH, halogen, carbonyl or other organic functional group; X and Y are H, Aryl, Alkyl, $CO_2R$ where R is an alkyl or aryl organic fragment 5. A method for making a linear polymer according to claim 1 wherein said ylid is selected from the group of ylids consisting of dimethyloxosulfonium methylide and triphenylarsonium benzylide.

6. A method for making a linear polymer according to claim 1 wherein said organoborane is selected from the group of alkylboranes consisting of trimethylborane, triethylborane, tri-n-hexylborane, tri-(2,4,4-trimethylpentyl)borane.

7. A linear polymer made according to the method set forth in claim 1.

8. A linear polymer made according to the method set forth in claim 3.

9. A method for making a linear polyalkylborane, said linear polyalkylborane comprising a backbone which comprises between about 25 and 10,000 carbon atoms, said method comprising the steps of:

reacting an amount of ylid with an amount of organoborane at a temperature which is sufficient to cause polyhomologation of said ylid and organoborane to form said polyalkylborane which comprises a carbon backbone, wherein the ratio of the amount of ylid to the amount of organoborane is selected such that the backbone of said polyalkylborane produced during said polyhomologation comprises between about 25 and 10,000 carbon atoms.

10. A method for making a linear polyalkylborane according to claim 9 wherein the ratio of the amount of ylid to the amount of organoborane is between 25 to 1 and 10,000 to 1.

11. A linear polyalkylborane made according to the method set forth in claim 9.

* * * * *